(12) United States Patent
Roy et al.

(10) Patent No.: US 9,078,808 B2
(45) Date of Patent: Jul. 14, 2015

(54) DEVICE TO DELIVER MAGNESIUM IN PEG FORMULATION

(75) Inventors: Josee Roy, Memphis, TN (US); Toya D. Kimble, Memphis, TN (US); Jeffery C. Marx, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 110 days.

(21) Appl. No.: 12/411,537

(22) Filed: Mar. 26, 2009

(65) Prior Publication Data

US 2010/0249699 A1    Sep. 30, 2010

(51) Int. Cl.
*A61J 1/20*    (2006.01)
*A61K 9/00*    (2006.01)
(Continued)

(52) U.S. Cl.
CPC .............. *A61J 1/2093* (2013.01); *A61J 1/2089* (2013.01); *A61K 9/0019* (2013.01); *A61K 33/06* (2013.01); *A61J 1/10* (2013.01); *A61J 2001/2027* (2013.01); *A61J 2205/20* (2013.01)

(58) Field of Classification Search
CPC ..... A61K 33/14; A61K 33/06; A61K 9/1075; A61K 9/0024; A61K 47/34; A61K 9/0019; A61K 9/1647; A61K 9/0014; A61K 9/2027; A61K 9/0056; A61K 9/2095; A61K 9/204; A61K 47/10; A61K 8/06; A61K 8/585; A61Q 19/00
USPC ...................... 604/84, 87, 86, 89, 92, 90, 416
See application file for complete search history.

(56) References Cited

U.S. PATENT DOCUMENTS

| 3,026,248 A | 3/1962 | Noseworthy et al. |
| 3,818,910 A * | 6/1974 | Harris .............................. 604/87 |
| 4,020,162 A * | 4/1977 | Ghilardi et al. ................ 514/153 |

(Continued)

FOREIGN PATENT DOCUMENTS

| DE | 3238649 A1 | 4/1984 |
| EP | 0295204 A1 | 12/1988 |

(Continued)

OTHER PUBLICATIONS

Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.

(Continued)

*Primary Examiner* — Nicholas Lucchesi
*Assistant Examiner* — Weng Lee
(74) *Attorney, Agent, or Firm* — Sorell Lenna & Schmidt LLP

(57) ABSTRACT

A container supplies a medicinal formulation that includes a hydrophilic polymer and an active agent capable of bonding to the polymer. The container includes a first compartment for storing the polymer and a second compartment fluidly isolated from the first compartment for storing the active agent. A frangible barrier is shared between the compartments. A fluidic outlet is disposed on the container to dispense the medicinal formulation. Dispensing of the medicinal formulation includes rupturing the frangible barrier, mixing the polymer and active agent together to form the medicinal formulation, and administering the medicinal formulation provided from the fluidic outlet to a patient. The polymer can be PEG, while the active agent can be magnesium.

20 Claims, 4 Drawing Sheets

(51) Int. Cl.
A61K 33/06 (2006.01)
A61J 1/10 (2006.01)

(56) References Cited

U.S. PATENT DOCUMENTS

| | | | | | |
|---|---|---|---|---|---|
| 4,131,200 | A | * | 12/1978 | Rinfret | 206/484 |
| 4,321,263 | A | * | 3/1982 | Powell et al. | 424/738 |
| 4,451,447 | A | | 5/1984 | Kaplan et al. | |
| 4,507,114 | A | * | 3/1985 | Bohman et al. | 604/111 |
| 4,602,910 | A | * | 7/1986 | Larkin | 604/87 |
| 4,608,043 | A | * | 8/1986 | Larkin | 604/87 |
| 5,330,978 | A | * | 7/1994 | Wakimasu et al. | 514/80 |
| 5,431,496 | A | * | 7/1995 | Balteau et al. | 383/38 |
| 5,605,687 | A | | 2/1997 | Lee et al. | |
| 5,877,224 | A | * | 3/1999 | Brocchini et al. | 514/772.2 |
| 6,302,574 | B1 | * | 10/2001 | Chan | 366/160.4 |
| 7,175,614 | B2 | * | 2/2007 | Gollier et al. | 604/410 |
| 7,582,680 | B1 | | 9/2009 | Shi et al. | |
| 7,837,987 | B2 | | 11/2010 | Shi et al. | |
| 2002/0164303 | A1 | * | 11/2002 | Finiels et al. | 424/93.2 |
| 2003/0104063 | A1 | * | 6/2003 | Babcock et al. | 424/486 |
| 2003/0118545 | A1 | | 6/2003 | Shi et al. | |
| 2004/0214790 | A1 | | 10/2004 | Borgens | |
| 2005/0069520 | A1 | | 3/2005 | Shi et al. | |
| 2007/0259044 | A1 | | 11/2007 | Roy et al. | |
| 2009/0166363 | A1 | | 7/2009 | Balteau | |
| 2010/0003679 | A1 | * | 1/2010 | Ichii et al. | 435/6 |

FOREIGN PATENT DOCUMENTS

| | | | |
|---|---|---|---|
| FR | 2859625 | A1 | 3/2005 |
| GB | 1250304 | A | 10/1971 |
| GB | 1286351 | A | 8/1972 |
| WO | 0128544 | A2 | 4/2001 |
| WO | 02092107 | | 11/2002 |

OTHER PUBLICATIONS

Borgens R B and Bohnert D., "Rapid recovery from spinal cord injury after subcutaneously administered polyetheylene glycol," Journal of Neuroscience Research (2001); vol. 66, pp. 1179-1186.

Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.

The International Search Report and the Written Opinion of the International Searching Authority in PCT/US2007/067580.

Turner, et al., "Magnesium gluconate offers no more protection than magnesium sulphate following diffuse traumatic brain injury in rats.", Journal of the American College of Nutrition. 23(5), (2004), 541S-544S.

Muir, et al., "Magnesium for acute stroke (Intravenous Magnesium Efficacy in Stroke trial): randomised controlled trial.", The Lancet, 363(9407), (Feb. 7, 2004), 439-45.

Saver, et al., "Prehospital Neuroprotective Therapy for Acute Stroke: Results of the Field Administration of Stroke Therapy-Magnesium (FAST-MAG) Pilot Trial.", Stroke, 35(5), (2004), 106-108.

Bittner, et al., "Reconnection of severed nerve axons with polyethylene glycol.", Brain Research, 367(1-2), (1986), 351-35.

McIntosh, et al., "Magnesium protects against neurological deficit after brain injury.", Brain Research, 482(2), (1989), 252-260.

Shapiro, et al., "Oscillating field stimulation for complete spinal cord injury in humans: a Phase 1 trial.", J. Neurosurg Spine, 2(1), (Jan. 2005), 3-10.

Resende, et al., "Local transcutaneous electrical stimulation (TENS) effects in experimental inflammatory edema and pain.", European Journal of Pharmacology, 504(1), (2004), 217-222.

Simpson et al., "Intrathecal magnesium sulfate protects the spinal cord from ischemic injury during thoracic aortic cross-clamping,"; Anesthesiology (1994) vol. 81, pp. 1493-1499.

Lang-Lazdunski et al., "Prevention of ischemic spinal cord injury: comparative effects of magnesium sulfate and riluzole,"Journal of Vascular Surgery (Jul. 2000); vol. 32; No. 1; pp. 179-189.

Ancill, R.J., "The blood volume of the normal guinea-pig," J. Physiol. (1956)l32, pp. 469-475.

Braun, Duplex® Drug Delivery System, B. Braun Medical Inc., Bethlehem, PA, 2008, 2 pgs.

U.S. Appl. No. 12/411,537, filed on Mar. 26, 2009.
U.S. Appl. No. 12/411,572, filed on Mar. 26, 2009.
U.S. Appl. No. 12/411,666, filed on Mar. 26, 2009.
U.S. Appl. No. 12/411,548, filed on Mar. 26, 2009.

International Search Report and Written Opinion for Application No. PCT/2010/028153 mailed on Jul. 7, 2010.

Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).

Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).

Kwon, et al. "Translational Research in Spinal Cord Injury: A Survey of Opinion from the SCI Community," Journal of Neurotrauma, 27, pp. 21-33 (Jan. 2010).

McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).

Journal of Spinal Cord Medicine, 34(6), 620-621 (2011).

* cited by examiner

DEVICE TO DELIVER MAGNESIUM IN PEG FORMULATION

FIELD OF THE INVENTION

The present invention relates generally to containers for dispensing medicaments. More particularly, the present invention discloses an IV bag having fluidly separated compartments, one of which is frangible to provide for mixing of materials respectively held in the compartments. More particularly still, the present invention discloses methods of administration and related IV bags that are suitable for the administration of a medication comprising a hydrophilic polymer and a metal ion.

BACKGROUND OF THE INVENTION

The use of intravenous (IV) bags in the administration of fluids to patients is well-known. A typical IV bag is made from a shell which defines a single fluidic compartment. Attached to the shell is a fluidic outlet in fluidic communications with the compartment and to which may be attached an IV line, using any standard attaching mechanism, such as any IV infusion set designed for either gravity or pump driven delivery.

It is often desirable to administer a combination of fluids to a patient. This is typically employed by using a respective IV bag for each fluid, and then connecting the respective IV line from each bag to a junction at which the two fluids combine to form a resultant mixture. An IV line from the junction then runs to the patient. This arrangement may be satisfactory for fluids that readily mix with each other, but is unsatisfactory for fluids that do not so readily mix, such as, for example, a particularly viscous fluid with another fluid. It also requires extra materials, such as the junction.

Accordingly, it would be desirable to have a single IV bag that permits a practitioner to administer to a patient a mixture of two fluids that are kept separated until just prior to administration.

SUMMARY OF THE INVENTION

In one embodiment, a container is disclosed to supply a medicinal formulation comprising a compound having hydrophilic properties and an active agent capable of bonding to the compound in an aqueous solution. The container includes a first compartment storing either the compound or the active agent, and a second compartment fluidly isolated from the first compartment for storing the other of the compound or the active agent. A frangible barrier is shared between the first compartment and the second compartment. A fluidic outlet is disposed on the container to dispense the medicinal formulation comprising at least the hydrophilic compound and the active agent.

In another embodiment, the first compartment, the second compartment, and the frangible barrier are formed within a shell, and the frangible barrier separates the first compartment from the second compartment. In such embodiment, the fluidic outlet is engaged with the shell.

In some embodiments, one or more of the compartments include a dye to provide for visual assistance of the mixing of the hydrophilic compound and active agent.

In some embodiments, the active agent comprises magnesium (Mg) and the compound comprises a hydrophilic polymer, for example, polyethylene glycol (PEG). In some embodiments, the resultant medicinal formulation after mixing comprises 10-60% of PEG and 0.1-20% of magnesium salt by weight (g) per 100 ml of the medicinal formulation.

In another embodiment, the first compartment is defined by a first shell, the second compartment is defined by a second shell, and the first and second shells are coupled to each other with a connector comprising one or more frangible barriers.

In still another embodiment, a method for administering a medicinal formulation dispensed from a preferred embodiment device is disclosed, which includes rupturing the frangible barrier, mixing the PEG and magnesium together to form the medicinal formulation, and administering the medicinal formulation provided from the fluidic outlet to a patient in need thereof.

In various embodiments, the medicinal formulation is administered to the patient at a dosage of about 0.5-10 ml/kg of the patient's body weight.

In various embodiments, the dosage is administered to the patient at a rate such that the dosage is administered within one half-life of PEG within the patient.

BRIEF DESCRIPTION OF THE DRAWINGS

In part, other aspects, features, benefits and advantages of the embodiments will be apparent with regard to the following description, appended claims and accompanying drawings where:

Figure 1:
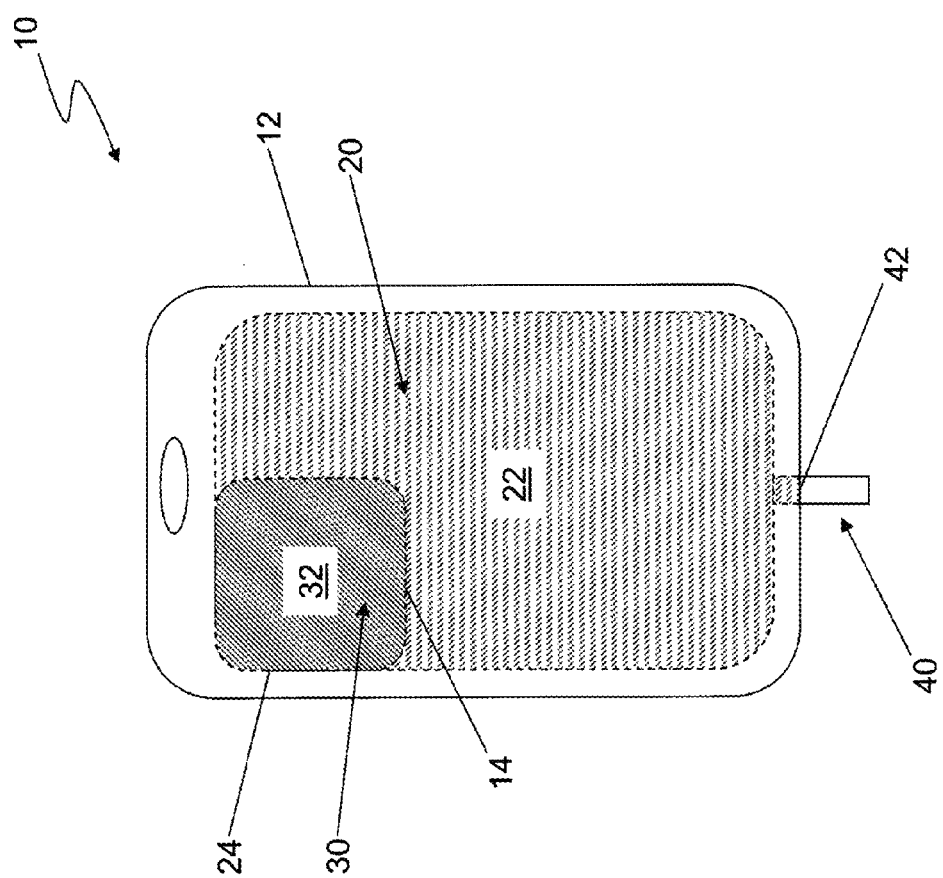
FIG. 1 is a side view of an embodiment IV bag in a first state.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

The term "patient" refers to a biological system to which a treatment can be administered. A biological system can include, for example, an individual cell, a set of cells (e.g., a cell culture), an organ, or tissue. Additionally, the term "patient" can refer to animals, including, without limitation, humans.

The term "treating" or "treatment" refers to executing a protocol, which may include administering one or more drugs, implants or the like to a patient (human or otherwise), in an effort to repair or alleviate signs or symptoms of a disease or condition. Alleviation can occur prior to signs or symptoms of the disease or condition appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

A "frangible barrier" in the following indicates any barrier or device that is used to separate two or more fluids from each other until mixing is desired, at which point the frangible barrier can be caused to no longer fluidly separate the two or more fluids from each other. For example, a film designed to rupture under pressure may provide a frangible barrier. Similarly, a valve may provide a frangible barrier, such as a pressure-release valve or a valve that opens in response to some other external stimulus. The frangible barrier may be activated by different forms of energy including, for example, gravity, pressure, suction, heat and combinations thereof. The frangible barrier may also be a component of or include a tubing connector. A tubing connector may be found within the container or as an external attachment to a container. Embodiment devices may contain one or more types of frangible barriers, connectors or combinations thereof.

For the sake of simplicity, in the following only mixtures comprising two fluids are discussed. It will be appreciated, however, that the methods and devices disclosed herein are applicable to mixtures of two or more fluids, solids or combinations thereof, using an appropriate number of frangible barriers and compartments.

For treatment purposes, it may be desirable to administer to a patient a medicinal formulation that is a mixture of two (or more) fluids. For efficacy purposes or other medical reasons, however, it may be desirable to keep these two components separated from each other until just prior to administration. By way of a specific example, a medicinal formulation may comprise a hydrophilic delivery polymer and at least one active agent where the interaction between the delivery polymer and the at least one active agent is mainly of an ionic nature. These interactions may be defined as a "chelation" like effect and, without wishing to be bound by theory, are based mainly on ionic interactions between the delivery polymer and the at least one active agent. For example, although polyethylene glycol (PEG) as a whole is non-ionic, the lone pairs of the electrons on the ether oxygens on the PEG chains impart an anionic character to the polymer and can bind to a cation such as $Mg^{2+}$ or $MgCl^{+}$. In some embodiments, the active agent may be selected from monodentate metal ions such as potassium and lithium, bidentate ions such as magnesium and calcium, transition metals including iron, zinc and copper as well as more complex ions like ammonium. Such metal ions are capable of forming complexes with the polymers by forming ionic bonds through electrostatic attraction to certain hetero atoms of the polymer, for example, N, O and S atoms. The type of ionic bond can vary including electron sharing between one or more metal molecule and one or more subunit present on one or more polymer molecules. The metal counterion may also participate in the formation of the complex with the delivery polymer.

Various embodiment devices form compositions that comprise hydrophilic compounds. Naturally occurring hydrophilic compounds include, but are not limited to: proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; methyl cellulose, sodium carboxylmethyl cellulose and activated polysaccharides such as dextran and starch derivatives.

Useful synthetic hydrophilic compounds include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), poly(polyethylene glycol methacrylate), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid, propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly (acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly (ethyloxazoline); and polyvinylamines.

The resultant mixture of a hydrophilic compound and an metal ion active agent may form medically useful "chelated" compounds. However, it has been observed that in some situations, over time, some of these mixtures may not be stable. For example, over time or under high temperature, such mixtures may form precipitates, which may be undesirable for administration purposes. To avoid these changes, it may therefore be desirable to create the mixture just prior to administration. For example, with specific reference to a medicinal mixture formed from a combination of PEG and Mg, it may be desirable to form the mixture immediately and up to 6 months before administration to the patient to avoid the formation of precipitates.

Many hydrophilic polymers, such as PEG, are quite viscous, and thus may require mechanical mixing to ensure that the ionic metal disperses evenly throughout the polymer. FIG. 1 illustrates an embodiment IV bag that supports the dual needs of fluidic separation with "just in time mixing". The IV bag 10 includes a shell 12 that defines a first compartment 20 into which is disposed a first fluid 22, such as PEG. The shells may be composed of materials comprising polyvinyl chloride (PVC), ethyl vinyl acetate (EVA), polyethylene (PE), fluorinated ethylene propylene (FEP), poly(tetrafluoroethylene) (PTEF), poly(tetrafluoroethene) (PTFE) or other suitable materials. These shells may be have an applied coating to reduce adherence or reactivity, modify gas or light permeability or otherwise improve the shell's performance such as but not limited to siliconization or the application of a second polymer film. A fluidic outlet 40 is connected to, or formed with, the shell 12 and is in fluidic communications with, or provides fluidic communications to, the first compartment 20. It will be appreciated that the fluidic outlet 40 may further include a frangible barrier 42, such as a film, valve or the like, to prevent leakage from the outlet 40 until administration for treatment purposes is desired. Alternatively, the fluidic outlet 40 may include a relatively permanent barrier 42 (i.e., one that is not easily broken or the like) that is designed to be punctured, such as by a cannula, to gain fluidic access to the first compartment 20. In either case, the fluidic outlet 40 is used as a dispensing point for a medicinal formulation provided, at least in part, from the IV bag 10.

A second compartment 30 is disposed within the first compartment 20 and is used to separately store a second fluid or solid 32. In some embodiments, the second compartment 30 stores an active agent that may be a monodentate metal ion, such as potassium and lithium; bidentate ions, such as magnesium and calcium; transition metals including iron, zinc and copper, as well as more complex ions such as an ammonium-containing fluid, and any combinations thereof. These solutions or solids may also contained buffers, dextrose, sodium chloride, preservatives and combinations thereof. In some embodiments, the second compartment 30 holds a Mg-containing fluid employing Mg as the active agent. The second compartment 30 fluidly isolates the second fluid 32 from the first fluid 22; that is, the second compartment 30 is fluidly isolated from the first compartment 20. In various embodiments, the second compartment 30 may be formed by a portion 24 of the sidewall of the first compartment 20 and by a separate fluidic barrier 14 connected to the perimeter of the sidewall portion 24. Alternatively, the fluidic barrier 14 may entirely define and enclose the second compartment 30. The fluidic barrier 14 is thus a shared barrier between the first compartment 20 and the second compartment 30.

In various embodiments, all or a portion of the fluidic barrier 14 is designed to rupture when under a pressure that exceeds a predefined or designed value. This pressure is preferably one that is not so low that unintended rupturing occurs, but not so great that an intended user, such as a medical practitioner, would find it difficult to cause the barrier 14 to rupture. Issues to consider when designing for this predefined pressure value, which it will be appreciated may be a range of values rather than a specific value, include expected stresses incurred in typical shipping and handling operations, and ease of use for the intended user. Ideally, the fluidic barrier 14 is designed to rupture before either the shell 12 ruptures or the barrier 42 ruptures. Thus, all or a portion of the fluidic barrier 14 provides a frangible barrier that, when ruptured, permits mixing of the second fluid 32 with the first fluid 22. By way of example, the fluidic barrier 14 may be a membrane made from the same material as the shell 12, but with a smaller thickness. Or, a portion of the surface of the fluidic barrier 14 may be scored, etched or the like to create regions of greater stress when under pressure, and thus regions which will fail earlier when under pressure. Alternatively, a relatively mechanically weaker material may be used for the fluidic barrier 14 than is used for the shell 12. Combinations of all of these variations are also possible.

Figure 2:
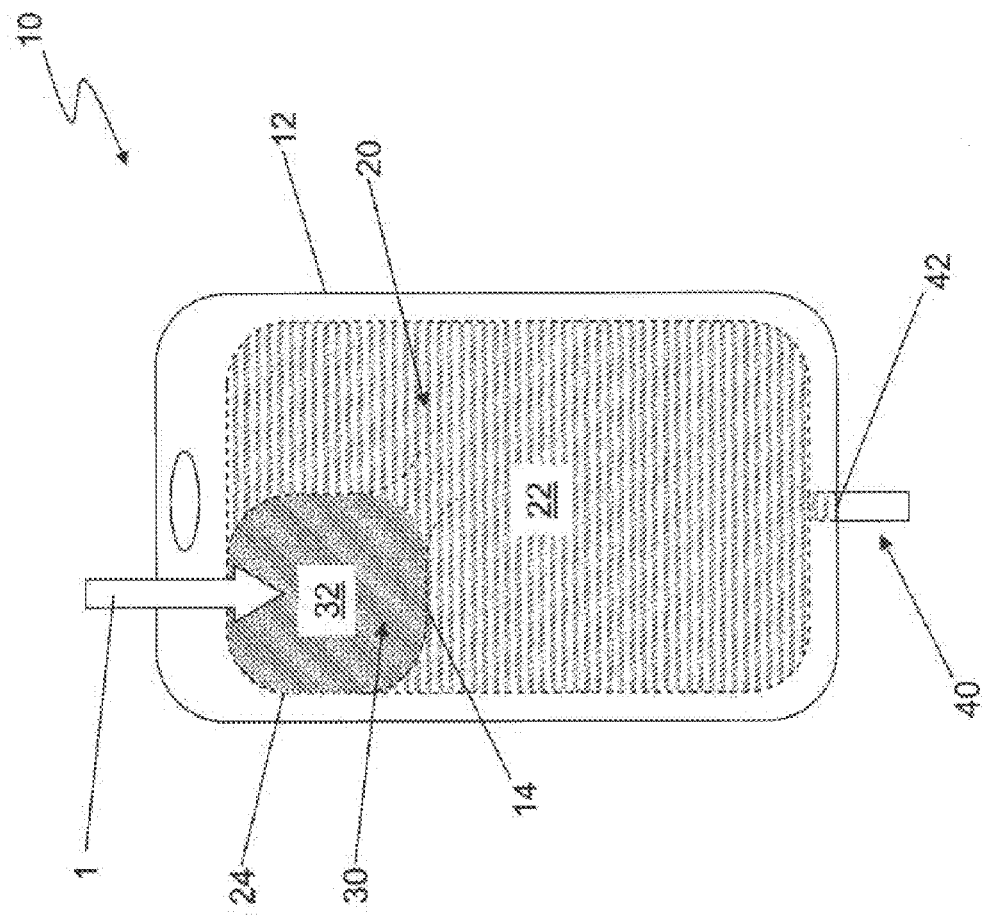
FIG. 2 is a side view of the IV bag shown in FIG. 1 in a second state prior to mixing.
Figure 3:
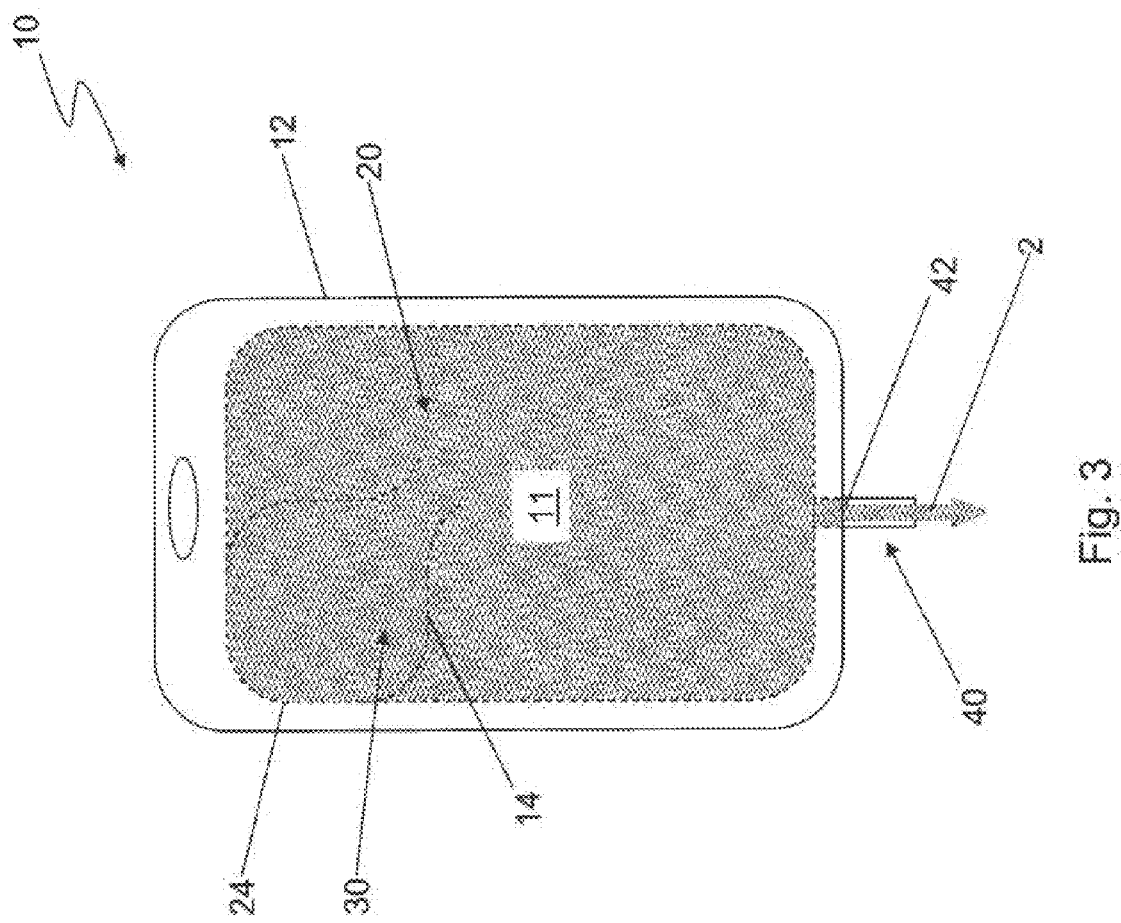
FIG. 3 is a side view of the IV bag shown in FIG. 2 after mixing.

As shown in FIG. 2, pressure, as indicated by arrow 1, may be placed upon the shared sidewall portion 24 of the shell 12, thus straining the second compartment 30. When the pressure 1 exceeds the predetermined or designed value, the frangible barrier provided by the fluidic barrier 14 ruptures, thereby fluidly connecting the first compartment 20 with the second compartment 30. The second fluid 32 and the first fluid 22 may then be evenly mixed together, such as by massaging the shell 12, shaking the IV bag 10, repeatedly inverting the IV bag 10, etc. As indicated by arrow 2 in FIG. 3, the resultant mixture 11 formed by mixing together the first fluid 22 with the second fluid 32 may then be dispensed through the fluidic outlet 40 in a standard manner for treatment purposes.

To ensure that adequate mixing has occurred between the first fluid 22 and the second fluid 32 to form the resultant mixture 11, either one of the first fluid 22 or the second fluid 32 may include a dye, although preferably the volumetrically smaller of the two includes the dye. For example, with specific reference to the embodiment IV bag 10 shown in FIG. 1, it may be preferable that the second fluid 32 includes the dye. Once the frangible barrier 14 ruptures, visual inspection of the dispersion of the dye throughout the volume of the other compartment, such as the first compartment 20, can provide evidence of adequate mixing between the fluids 22, 32. In this manner, "hot spots" of, for example, the Mg-containing component in the second fluid 32, such as PEG, are avoided in the mixture 11. To provide even better visual evidence of adequate mixing, both the first fluid 22 and the second fluid 32 may include a respective dye. Preferred dyes are visually distinct from each other, so that the resultant mixture 11 has a color that is different from either of the dyes used in the first fluid 22 and the second fluid 32. For example, the first fluid 22 may be colored with a blue dye, and the second fluid 32 may be colored with a yellow dye. In this manner, local hot spots in either of the fluids 22, 32 may be more easily visualized. Non-limiting examples of dyes include FDA certifiable color additives such as FD&C (Food, Drug and Cosmetic) or D&C (Drug and Cosmetic) dyes (water soluble but not oil soluble) and lakes (combination of dyes and insoluble material, not oil soluble but which are oil dispersible), Blue No. 1 (Brilliant Blue FCF, E133 MW 792.84), Blue No. 2 (Indigotine, E132 MW 466.35), Green No. 3 (Fast Green FCF, E143 MW 808.84), Red No. 40 (Allura Red AC, E129 MW 496.43), Red No. 3 (Erythrosine, E127 MW 879.86), Yellow No. 5 (Tartrazine, E102 MW 534.36), Yellow, No. 6 (Sunset Yellow FCF, E110 MW 534.36), Orange B (C.I. Acid Orange 137 540.49), Citrus Red No. 2 (C.I. Solvent Red 80, C.I. 12156 MW 308.33)) and methylene blue trihydrate (MW 373.9).

Figure 4:
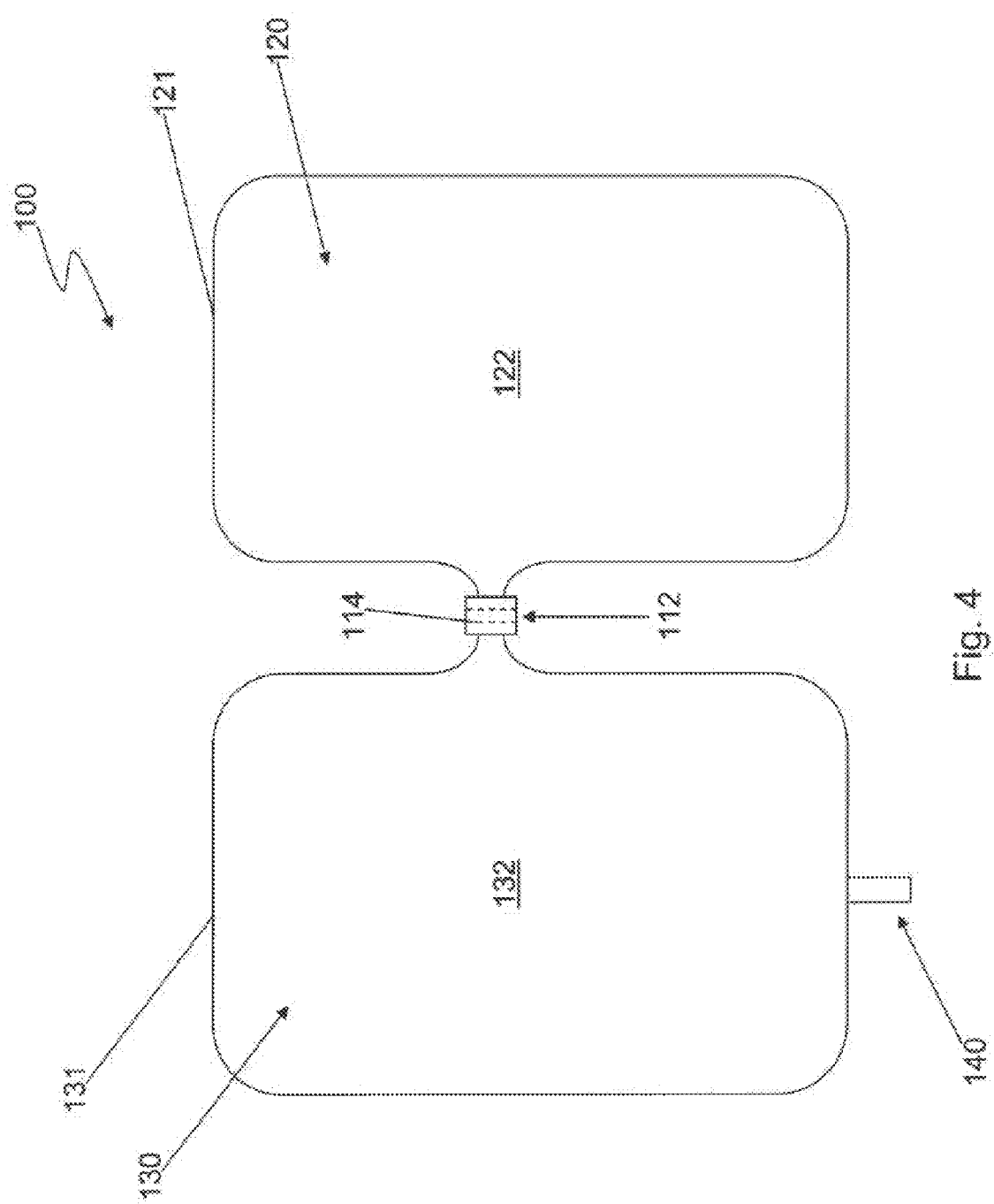
FIG. 4 shows another embodiment container.

FIG. 4 illustrates another embodiment container 100. The container 100 includes a first compartment 120 for storing a first fluid 122, such as PEG, and a second compartment 130 for storing a second fluid 132, such as a Mg-containing fluid. The second compartment 132 is fluidly connected to a fluidic outlet 140. Each compartment 120, 130 may be defined by a respective shell 121, 131. The compartments 122, 132 and their respective shells 121, 131 may be mechanically and fluidly joined to each other via connector 112. The connector 112 may be found within the device 100 formed by the two shells 121, 131, or may be applied externally to link the two shells 121, 131. As shown, in some embodiments the connector 112 may be located external to the shells 121, 131, and each shell 121, 131 may include a portion of the total connector 112 which are then linked together to form the connector 112. Any suitable connector 112 may be used, and may permanently or releasably connect the first shell 121 to the second shell 131. For example, the connector 112 may include plastic, glass or rubber tubing with or without coatings to reduce adherence or reactivity, such as but not limited to siliconization, that allows for the fluid to flow from one shell 121, 131 to the other one 131, 121. Internally, the connector includes at least one frangible barrier 114 that fluidly separates the first fluid 122 from the second fluid 132. The frangible barrier 114 may be a membrane or a valve that is activated by some energy source including manual force, pressure, gravity, suction or heat. There may be one frangible barrier 114 in the middle of the connector 112, or there may be one frangible barrier 114 at each extremity of the connector 112. Hence, the barrier or barriers 114 are shared between the first compartment 120 and the second compartment 130 to fluidly isolate these compartments 120, 130 from each other. When sufficient pressure or other energy source is applied to either one of the compartments 120, 130, or connector 112, the frangible barrier(s) 114 break or release, thereby fluidly coupling the first compartment 120 with the second compartment 130. The first fluid 122 and the second fluid 132 may thus be mixed together via the connector 112. For example, the fluids 122, 132 may be squeezed back and forth between the compartments 120, 130 via the connector 112 to facilitate complete mixing. The resultant mixture may then be dispensed in a standard manner from the fluidic outlet 140. As in the previous embodiment 10, either one or both of the fluids 122, 132 may include a dye to facilitate visual confirmation that adequate mixing has occurred.

In some embodiments, the device is used to deliver a formulation comprising PEG as a hydrophilic polymer compound and magnesium as an active agent. In such embodiments, one compartment may contain an aqueous solution of a PEG-containing fluid and the other compartment may contain magnesium powder. In such embodiments, the frangible barrier and/or connector allows for the PEG solution to contact and dissolve the magnesium powder. Alternatively, in other embodiments, a diluent may be added to the magnesium powder before it is mixed with the PEG-component. In yet other embodiments, the magnesium is provided as a solution. In yet other embodiments, a diluent may be added to the magnesium powder and the same or a different diluent may be added to a PEG powder before the two solutions are mixed by way of the frangible barrier.

Hydrophilic compounds, such as polymers, used with the present invention preferably have a half-life in the patient of less than 3 hours, and more preferably less than 2 hours, and most preferably less than 1 hour. The rate of excretion, or half-life, of a polymer is related to the molecular weight of the polymer, with higher molecular weight polymers having longer half-lives. Furthermore, for the same molecular weight, hydrophilic polymers have shorter half-lives than more hydrophobic polymers. Hydrophilic polymers that can be excreted mostly unchanged through urine have shorter half-lives than polymers that require some transformation before excretion. For example, it is understood that 24,000 DA is the approximate cut-off for glomerular filtration, and hence any polymer heavier than 24,000 DA needs to be degraded to some extent before it can be excreted, which adds to its half-life. Accordingly, delivery polymers may be selected from polymers with hydrophilic properties having a molecular weight of less than about 24,000 DA. Some embodiments employ PEG with molecular weights of between about 100 and 20,000 DA, more preferably between about 300 to 9000 DA, and most preferably still between about 2,000 DA and about 4,000 DA. PEGs of various molecular weights may be obtained from, for example, Sigma-Aldrich, St. Louis, Mo., USA.

In one embodiment, various magnesium salts may be used as a source for magnesium as the active agent. Suitable magnesium salts include, but are not limited to, magnesium sulfate, magnesium carbonate, magnesium chloride, magnesium oxide and magnesium hydroxide or any combination thereof. These compounds are readily available commercially from, for example, Sigma Aldrich, St. Louis, Mo., USA.

In some embodiments, the compartments in an embodiment device are respectively loaded with a polymer (preferably PEG) and an active agent (preferably Mg) so that the medicinal formulation finally dispensed from the fluidic outlet has a concentration of the delivery polymer from between about 10 to 60% weight per volume, i.e. 10 gm to 60 gm of polymer to 100 ml solution, preferably between about 20 and about 40% weight per volume, and most preferably between about 30% and about 40% weight per volume. The medicinal formulation finally formed and dispensed preferably comprises between about 10% to 60% of the polymer and about 0.1% to about 20% of the active agent, and more preferably between 0.1 and 10% of the active agent, and most preferably between about 0.4 and 4% of the active agent all in percentages of weight per volume (i.e. g of polymer or active agent per 100 ml of solution to be administered). The concentration of the delivery polymer in the medicinal formulation may depend on the number of chelation sites in the delivery polymer.

Embodiment devices may be used to provide medicinal formulations provided by the mixing of the components within their compartments and dispensing the resultant medicinal formulation to a patient in need thereof. Any suitable means may be used to provide the medicinal formulation dispensed from the fluidic outlet to the patient, such as an IV line together with an optional intermediate fluidic pump. For medicinal formulations dispensed from the fluidic outlet, a patient generally needs to receive a dose of at least about 0.5 to about 20 ml of the formulation per kg of the patient's body weight, more preferably between about 0.5 and 10 ml and most preferably between about 1 and 8 ml of the formulation per kg of the patient's body weight. In one embodiment, the patient receives a dose of 0.1 to 3 g of PEG3350 and 4 to 80 mg of magnesium chloride hexahydrate per kg of the patient's body weight, and most preferably between about 0.3 to 2.5 g of PEG3350 and 8 to 65 mg of magnesium chloride hexahydrate per kg of the patient's weight. A repeat dose may be administered if necessary. It will be appreciated, then, that the total volume of medicinal formulation provided by an embodiment device, and hence the respective volumes of the first and second compartments, may depend upon the expected body mass of the target patient.

As noted above, medicinal formulations are rapidly excreted from the patient. Because such hydrophilic polymers are likely to have a short half life in the body, they are ideally administered to a patient rapidly. More specifically, it may be desirable to administer a dose of a medicinal formulation to a patient within two half-lives, and more preferably within one half-life, of the medicinal formulation. Consider, for example, a medicinal formulation that employs as a hydrophilic compound PEG having a molecular weight of between 1000 and 6000 Da. The half-lives of such PEGs are between about 30 and about 90 minutes in humans, and thus it is desirable to administer a dose of such a resultant medicinal formulation comprising such PEGs within about 180 minutes to take in account individual variability, more preferably within 90 minutes. Hence, in situations or for medicinal formulations where gravity is insufficient to provide the desired flow rate from the device to the patient, an intermediate pump may be used to urge dispensing of the medicinal formulation from the fluidic outlet and into the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A container to supply a medicinal formulation to a patient in need thereof, the container comprising:
    a medicinal formulation comprising:
        polyethylene glycol (PEG) comprising PEG3350 in an amount ranging from 10% to 60% by weight (g) per 100 ml volume of the medicinal formulation;
        up to 80 mg of a magnesium chloride per kg of said patient's weight, and the magnesium chloride is present in an amount ranging from 0.1 to 20% by weight (g) of magnesium per 100 ml volume of the medicinal formulation; and
        an aqueous solution,
    a first compartment storing either the PEG or the magnesium chloride of the medicinal formulation;
    a second compartment disposed within the first compartment such that the second compartment is fluidly isolated from the first compartment, the second compartment storing the other of the PEG or the magnesium chloride of the medicinal formulation;
    at least one first frangible barrier shared between the first compartment and the second compartment, wherein the first and second compartments each comprise an outer perimeter and the outer perimeter of the first compartment and the outer perimeter of the second compartment intersect one another such that the second compartment is disposed at the outer perimeter of the first compartment; and
    a fluidic outlet for dispensing from the container the medicinal formulation, the fluidic outlet comprising at least one second frangible barrier disposed therein,
    wherein rupturing said at least one first frangible barrier causes the content of said first and second compartments to mix producing said medicinal formulation such that said medicinal formulation is stable for up to 6 months before administration to said patient.

2. A method for administering a medicinal formulation dispensed from the device of claim 1, the method comprising:
    rupturing the at least one first frangible barrier;
    causing the PEG and magnesium chloride to become substantially uniformly mixed with each other; and
    administering at least the resultant medicinal formulation provided from the fluidic outlet to a patient in need thereof.

3. The method of claim 2 wherein the medicinal formulation is administered to the patient at a dosage of about 0.5 to 10 ml/kg of the patient's body weight.

4. The method of claim 3 wherein the dosage is administered to the patient at a rate such that the dosage is administered within one half-life of PEG within the patient.

5. The container of claim 1 wherein the first compartment, the second compartment, and the at least one first frangible barrier are formed within a shell, the at least one first frangible barrier separates the first compartment from the second compartment, and the fluidic outlet is engaged with the shell.

6. The container of claim 5 wherein the at least one first frangible barrier is a membrane.

7. The container of claim 1 wherein the first compartment comprises a first dye having a first color.

8. The container of claim 7 wherein the second compartment comprises a second dye having a second color that is substantially visually different from the first color.

9. The container of claim 1 wherein the first compartment is defined by a first shell, the second compartment is defined by a second shell, and the first and second shells are coupled to each other.

10. The container of claim 1 wherein the first compartment and the second compartment each have a substantially rectangular configuration.

11. The container of claim 1 wherein the first compartment is disposed within a shell, and the shell and the at least one first frangible barrier are made from the same material.

12. The container of claim 1 wherein the first compartment is disposed within a shell, the at least one first frangible barrier is made from a first material and the shell is made from a second material that is different from the first material, the first material being weaker than the second material.

13. The container of claim 1 wherein the at least one first frangible barrier is scored or etched to create regions of greater stress when under pressure.

14. The container of claim 1 wherein the first compartment comprises a center portion and the second compartment is offset from the center portion.

15. A container to supply a medicinal formulation to a patient in need thereof, the container comprising:
    a medicinal formulation comprising:
        polyethylene glycol (PEG) comprising PEG3350 in an amount ranging from 10% to 60% by weight (g) per 100 ml volume of the medicinal formulation;
        up to 80 mg of a magnesium chloride per kg of said patient's weight, and the magnesium chloride is present in an amount ranging from 0.1 to 20% by weight (g) of magnesium per 100 ml volume of the medicinal formulation; and
        an aqueous solution,
    a first compartment storing either the PEG or the magnesium chloride of the medicinal formulation;
    a second compartment spaced apart from the first compartment, the second compartment storing the other of the PEG or the magnesium chloride of the medicinal formulation;
    a connector linking the first compartment and the second compartment, the connector comprising at least one first frangible barrier to fluidly separate the first and second compartments; and
    a fluidic outlet for dispensing from the container the medicinal formulation, the fluidic outlet comprising at least one second frangible barrier disposed therein,
    wherein rupturing said at least one first frangible barrier causes the content of said first and second compartments to mix producing said medicinal formulation such that said medicinal formulation is stable for up to 6 months before administration to said patient.

16. A method for administering a medicinal formulation dispensed from the device of claim 15, the method comprising:
    rupturing the at least one first frangible barrier;
    causing the PEG and magnesium chloride to become substantially uniformly mixed with each other; and administering at least the resultant medicinal formulation provided from the fluidic outlet to a patient in need thereof.

17. The container of claim 15 wherein the at least one first frangible barrier is a single frangible barrier positioned in a middle portion of the connector.

18. The container of claim 15 wherein the at least one first frangible barrier comprises one frangible barrier in a first end of the connector in communication with the first compartment and another frangible barrier positioned within a second end of the connector opposite the first end in communication with the second compartment.

19. The container of claim 1, wherein the PEG is in an amount of 0.3 to 2.5 g per kg of said patient's weight and the magnesium is in an amount of 8 to 65 mg per kg of said patient's weight.

20. The container of claim 15, wherein the PEG is in an amount of 0.3 to 2.5 g per kg of said patient's weight and the magnesium is in an amount of 8 to 65 mg per kg of said patient's weight.

* * * * *